United States Patent [19]
Viegas et al.

[11] Patent Number: 5,300,295
[45] Date of Patent: Apr. 5, 1994

[54] OPHTHALMIC DRUG DELIVERY WITH THERMOREVERSIBLE POLYOXYALKYLENE GELS ADJUSTABLE FOR PH

[75] Inventors: Tacey X. Viegas; Lorraine E. Reeve, both of Ann Arbor; Robert S. Levinson, Saline, all of Mich.

[73] Assignee: Mediventures, Inc., Grosse Pointe Park, Mich.

[21] Appl. No.: 759,234

[22] Filed: Sep. 13, 1991

Related U.S. Application Data

[63] Continuation-in-part of Ser. No. 517,273, May 1, 1990, abandoned.

[51] Int. Cl.$^5$ .................... A61K 9/10; A61K 47/34
[52] U.S. Cl. .................... 424/427; 424/486; 514/944; 514/912; 523/105; 523/122; 252/315.1
[58] Field of Search .................... 424/427, 28.37, 486; 514/944, 954, 912–915, 772.1; 523/109, 111, 122; 252/315.1

[56] References Cited

U.S. PATENT DOCUMENTS

| | | | |
|---|---|---|---|
| 2,677,700 | 5/1954 | Jackson et al. | 424/56 |
| 3,535,307 | 10/1970 | Moss et al. | 521/167 |
| 3,829,506 | 8/1974 | Schmolka et al. | 528/77 |
| 4,188,373 | 2/1980 | Krezanoski | 428/78 |
| 4,255,415 | 3/1981 | Chrai et al. | 424/606 |
| 4,474,751 | 10/1984 | Haslam et al. | 424/78 |
| 4,474,752 | 10/1984 | Haslam et al. | 424/78 |
| 4,474,753 | 10/1984 | Haslam et al. | 424/78 |
| 4,478,822 | 10/1984 | Haslam et al. | 424/78 |
| 4,810,503 | 3/1989 | Carson et al. | 424/76.3 |
| 4,879,109 | 11/1989 | Hunter | 424/83 |

*Primary Examiner*—Edward Webman
*Attorney, Agent, or Firm*—Dykema Gossett

[57] ABSTRACT

Aqueous gel drug delivery compositions and medical devices, useful for treating an eye condition, having hyperosmotic, iso-osmotic or hypo-osmotic characteristics in the gel state, are obtained by calculating the osmolality required in the liquid state to reach a desired osmotic force in the gelled state by assuming that a polyoxyalkylene block copolymer does not contribute to the osmolality in the gel state.

23 Claims, 1 Drawing Sheet

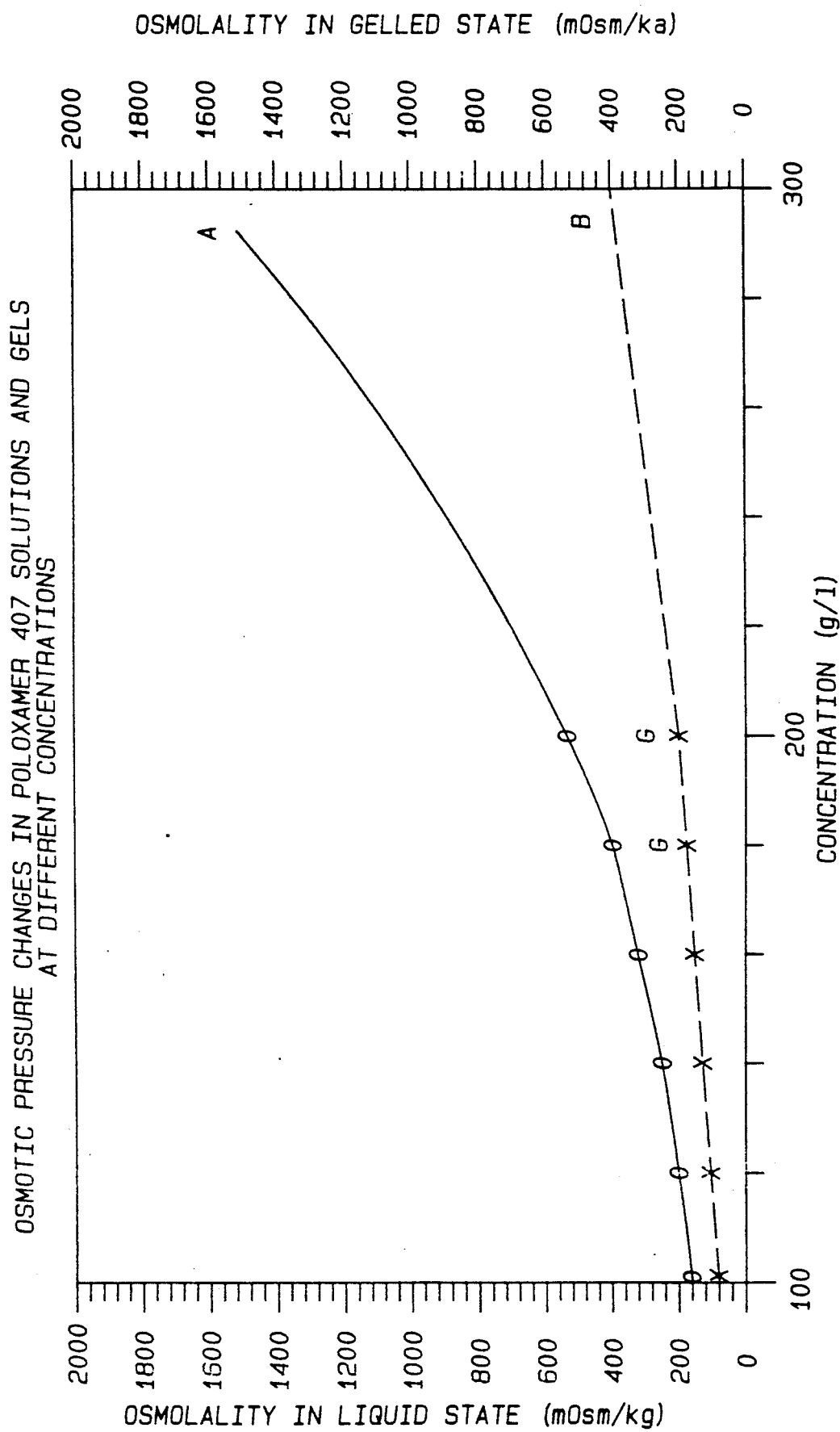

OPHTHALMIC DRUG DELIVERY WITH THERMOREVERSIBLE POLYOXYALKYLENE GELS ADJUSTABLE FOR PH

This is a continuation-in-part of copending application Ser. No. 07/517,273 filed on May 1, 1990 abandoned.

BACKGROUND OF THE INVENTION

1. Field of the Invention

This invention relates to ophthalmic drug delivery vehicles, drug delivery compositions, and medical devices comprising an aqueous gel.

2. Description of the Prior Art

Over the years, methods have been developed to achieve the efficient delivery of a therapeutic drug to a mammalian body part requiring pharmaceutical treatment. Use of an aqueous liquid which can be applied at room temperature as a liquid but which forms a semisolid gel when warmed to body temperature has been utilized as a vehicle for drug delivery since such a system combines ease of application with greater retention at the site requiring treatment than would be the case if the aqueous composition were not converted to a gel as it is warmed to mammalian body temperature. In U.S. Pat. No. 4,188,373, PLURONIC ® polyols are used in aqueous compositions to provide thermally gelling aqueous systems. Adjusting the concentration of the polyol provides the desired sol-gel transition temperature, that is, the lower the concentration of polyol, the higher the sol-gel transition temperature; after crossing a critical concentration minimum, below which a gel will not form.

In U.S. Pat. No. 4,474,751; '752; '753; and 4,478,822 drug delivery systems are described which utilize thermosetting gels; the unique feature of these systems is that both the gel transition temperature and/or the rigidity of the gel can be modified by adjustment of the pH and/or the ionic strength, as well as by the concentration of the polyol.

Other patents disclosing pharmaceutical compositions which rely upon an aqueous gel composition as a vehicle for the application of the drug are U.S. Pat. Nos. 4,883,660; 4,767,619; 4,511,563; and 4,861,760. Thermosetting gel systems are also disclosed for application to injured mammalian tissues of the thoracic or peritoneal cavities in U.S. Pat. No. 4,911,926.

While the prior art is silent with respect to the isotonicity of aqueous drug delivery vehicles and medical devices, osmotic drug delivery systems are disclosed in U.S. Pat. No. 4,439,196 which utilize a multi-chamber compartment for holding osmotic agents, adjuvants, enzymes, drugs, pro-drugs, pesticides, and the like. These materials are enclosed by semipermeable membranes so as to allow the fluids within the chambers to diffuse into the environment into which the osmotic drug delivery system is in contact. The drug delivery device can be sized for oral ingestion, implantation, rectal, vaginal, or ocular insertion for delivery of a drug or other beneficial substance. Since this drug delivery device relies on the permeability of the semipermeable membranes to control the rate of delivery of the drug, the drugs or other pharmaceutical preparations, by definition, are not isotonic with mammalian blood.

SUMMARY OF THE INVENTION

Drug delivery vehicles, drug delivery compositions, and medical devices are disclosed. The pharmaceutical compositions contain pharmacologically active medicaments useful in providing treatments to ophthalmic areas of the mammalian body requiring pharmacological treatment or requiring the administration of a diagnostic agent. The use of compositions of the invention as medical devices is indicated where an aqueous gel is desirable to cover injured tissue or separate delicate tissues in a manner more gentle than can be accomplished using surgical instruments. The compositions can be adjusted to be hyperosmotic, iso-osmotic, or hypo-osomtic and, in one embodiment of the invention, provide a physiologically acceptable media having a buffered pH and an osmotically balanced vehicle so as to, preferably, provide a mixture which is iso-osmotic with body fluids and which has a pH similar to bodily fuids, such as lacrimal tears. The pH and osmotic pressure of lacrimal tears is about pH 7.4 and 290 mosm/kg. In addition, the compositions of the invention are, optionally, sterilized so as to insure that the compositions of the invention do not provide a source of infection. The drug delivery vehicles and medical devices can be adjusted to the desired osmolality by assuming that a polyoxyalkylene block copolymer present therein does not contribute to the osmolality in the gel state.

Polyphase systems are also useful and may contain non-aqueous solutes, non-aqueous solvents, and other non-aqueous additives. Homogeneous, polyphase systems can contain such additives as water insoluble high molecular weight fatty acids and alcohols, fixed oils, volatile oils and waxes, mono-, di-, and triglycerides, and synthetic, water insoluble polymers without altering the functionality of the system.

In a preferred embodiment, the compositions of the invention can be delivered to the area of the mammalian body requiring treatment as a low viscosity liquid at ambient temperatures which, upon contact with the mammalian body, forms a semisolid gel having a very high viscosity. Because the preferred compositions of the invention are low viscosity liquids at ambient temperatures, they easily pass to various ophthalmic areas insuring maximum contact between exposed tissue and, for instance, the pharmaceutical compositions of the invention. If necessary, the compositions of the invention can be washed away under a gentle stream of cool water, thus minimizing the risk of further injury and pain to the patient upon removal.

A wide variety of polyoxyalkylene copolymers are suitable for the preparation of the compositions of the invention. Generally, it is necessary to adjust the copolymer concentration in aqueous solution so as to obtain the desired sol-gel transition temperature in order that the compositions can be provided as low viscosity liquids at ambient temperature, yet form semisolid gels at mammalian body temperatures. In addition to the concentration of the copolymer, other suitable excipients may be added so as to provide the desired osmotic properties.

The useful copolymers which provide the sol-gel characteristics of the pharmaceutical compositions of the invention are, preferably, polyoxyalkylene block copolymers.

DESCRIPTION OF THE DRAWING

The drawing provides a curve showing the osmolality in the solution state of a polyoxyalkylene copolymer, identified as Poloxamer 407, at various concentrations in a 0.1 molar TRIS hydrochloride buffer. The scale at the left side of the plot indicates the osmolality in the liquid state, while the scale on the right side of the plot indicates the osmolality of the composition when in the gelled state. Thus, curve A provides a graph showing the osmolality in the liquid state at various concentrations in grams per liter of the Poloxamer 407. Curve B shows the osmolality calculated for the gel state. Curve A is obtained by measuring the effect upon the freezing point depression of the Poloxamer 407 solutions in comparison with a sample of purified water (deionized water). It is noted that the curves were obtained by fitting the osmolality and concentration of polymer to the quadratic equation, $Y=A+Bx+Cx^2$, where Y is osmolality, x is concentration, and A, B, and C are constants. The relationship of concentration to osmolality is nonlinear in this system.

DETAILED DESCRIPTION OF THE INVENTION

It has been found that aqueous pharmaceutical vehicles or medical devices containing a polyoxyalkylene block copolymer, which have the unique feature, in a preferred embodiment, of being liquid at ambient temperatures and transitioning at mammalian body temperatures to a semisolid gel, can be made isotonic or iso-osmotic (or hyperosmotic or hypo-osmotic) and adjusted to the pH of mammalian body fluids, such as lacrimal tears. The pH and osmotic pressure of such bodily fluids are 7.4 and 290 mOsm/kg, respectively. It is, accordingly, advantageous to deliver a pharmacologically active medicament to an area of the mammalian body requiring pharmacological treatment under pH and osmotic pressure conditions which match those of bodily fluids. Optionally, the pharmaceutical compositions of the invention can be provided in a sterile condition.

In addition to those polyoxyalkylene copolymers described above, which are suitable in the formation of the pharmaceutical compositions of the invention, other polyoxyalkylene copolymers which form gels at low concentrations in water are suitable. One such copolymer is described in U.S. Pat. No. 4,810,503, incorporated herein by reference. These copolymers are prepared by capping conventional polyether polyols with an alpha-olefin epoxide having an average of about 20 to about 45 carbon atoms, or mixtures thereof. Aqueous solutions of these copolymers gel in combination with surfactants, which can be ionic or nonionic. The combination of the capped polyether polyols and the surfactants provide aqueous gels at low concentrations of the capped polyol and surfactant, which generally do not exceed 10% by weight total. Detailed methods of preparing these aqueous gels are disclosed in U.S. Pat. No. 4,810,503. Preparation of said aqueous gels is generally described below. Preferred surfactants for use in preparing these gels are also disclosed in said patent.

A conventional copolymer polyether polyol is prepared by preparing block or heteric intermediate polymers of ethylene oxide and at least one lower alkylene oxide having 3 to 4 carbon atoms as intermediates. These are then capped with the alpha-olefin epoxide to prepare the polymers. Ethylene oxide homopolymers capped with said alpha-olefin oxides are also useful as intermediates.

The heteric copolymer intermediate is prepared by mixing ethylene oxide and at least one lower alkylene oxide having 3 to 4 carbon atoms with a low molecular weight active hydrogen-containing compound initiator having at least two active hydrogens and preferably, 2 to 6 active hydrogen atoms such as a polyhydric alcohol, containing from 2 to 10 carbon atoms and from 2 to 6 hydroxyl groups, heating said mixture to a temperature in the range of about 50° C. to 150° C., preferably from 80° C. to 130° C., under an inert gas pressure preferably from about 30 psig to 90 psig.

A block copolymer intermediate is prepared by reacting either the ethylene oxide or said alkylene oxide having 3 to 4 carbon atoms with said active hydrogen-containing compound followed by reaction with the other alkylene oxide.

The ethylene oxide and the alkylene oxides having from 3 to 4 carbon atoms are used in said intermediates in amounts so that the resulting polyether product will contain at least 10 percent by weight, preferably about 70 percent to about 90 percent by weight, ethylene oxide residue. The ethylene oxide homopolymer intermediate is prepared by reacting ethylene oxide with said active hydrogen-containing compound. The reaction conditions for preparing the block copolymer and ethylene oxide homopolymer intermediates are similar to those for the heteric copolymer intermediate. The temperature and pressure are maintained in the above ranges for a period of about one hour to ten hours, preferably one to three hours.

The alpha-olefin oxides which are utilized to modify the conventional polyether intermediate of the prior art are those oxides and the commercially available mixtures thereof generally containing an average of about 20 to 45, preferably about 20 to 30, carbon atoms. The amount of alpha-olefin required to obtain the more efficient capped polyethers is generally about 0.3 to 10 percent, preferably about 4 to 8 percent, of the total weight of the polyethers.

Since the preparation of heteric and block copolymers of alkylene oxides and ethylene oxide homopolymers are well known in the art, further description of the preparation of said copolymers is unnecessary. Further details of the preparation of heteric copolymers of lower alkylene oxide can be obtained in U.S. Pat. No. 3,829,506, incorporated herein by reference. Further information on the preparation of block copolymers of lower alkylene oxides can be obtained in U.S. Pat. Nos. 3,535,307; 3,036,118; 2,979,578; 2,677,700; and 2,675,619 incorporated herein by reference.

The surfactants may be ionic or non-ionic and many surfactants and types of surfactants may be employed. While all surfactants may not be effective in the preparation of the isotonic gels of the instant invention, the fact that many are effective makes it a simple matter for one skilled in the art to select such surfactant with a minimum of trial and error.

The amounts of capped polyether copolymer and surfactant may be as little as 1.0 percent by weight or less of each depending on the type and amount of the other component. There appears to be no maximum amount of either component than that dictated by economic considerations. However, the total amount of capped copolymer and surfactant would generally not exceed 10 percent by weight.

With specific reference to the use of the pharmaceutical compositions as ophthalmic drug delivery compositions, it is noted that for the avoidance of adverse physiological effects to the eye, it is desirable that the pH and osmolality of the pharmaceutical vehicle be matched to the pH and osmolality of the eye. However, any desired pH and osmolality can be provided, for instance, the compositions of the invention can be formulated so as to be hyperosmotic or hypo-osomtic to mammalian body tissues. In addition, it is noted that a large percentage of drugs administered to the eye are lost as a result of lacrimal drainage. This applies especially in situations in which a liquid composition containing a pharmacologically active medicament is applied to the cornea of the eye. Accordingly, in such cases, only a small fraction of the pharmaceutical composition administered to the eye remains in contact with the cornea for a few minutes and an even smaller fraction penetrates into the cornea. To overcome these disadvantages, it is known to use viscous solutions, gels, ointments, or solid eye implants containing pharmacologically active medicaments. While progress has been made in the delivery of drugs by the use of solid implants, many patients find it difficult to tolerate the introduction of the implants into the conjunctival areas.

To solve this problem, drug delivery systems which are liquid at room temperature and assume a semisolid form at human body temperature have been proposed, such as those described in U.S. Pat. No. 4,188,373, which disclose the use of PLURONIC ® polyols. In U.S. Pat. No. 4,861,760 and U.S. Pat. No. 4,474,751, ophthalmic drug delivery systems are disclosed which show liquid-gel phase transitions. In the '751 patent, polymers are disclosed which are tetra substituted derivatives of ethylenediamine, propylenediamine, butylenediamine, pentylenediamine, or hexylenediamine. These are described as block copolymers of poly(oxypropylene) and poly(oxyethylene) of various chain lengths. These copolymers are utilized as aqueous drug delivery vehicles which contain from 10% to 50% by weight of copolymer based on the weight of the total drug delivery vehicle. In the '760 patent, the liquid-gel phase transition compositions for ophthalmological use contain copolymers which form gels at concentrations 10-100 fold lower than those used in systems such as the '751 patent, involving thermogellation. Accordingly, the drug delivery systems of the '760 patent are said to be very well tolerated by the eye. The polymers utilized in the drug delivery vehicles of the '760 patent are described as polysaccharides obtained by fermentation of a microorganism.

Generally, the polyoxyalkylene block copolymers of the invention are defined as follows:

a polyoxyalkylene block copolymer of the formula

$$[Y(A)_n-E-H]_x \quad (I)$$

wherein A is a polyoxyalkylene moiety having an oxygen/carbon atom ratio of less than 0.5, x is at least 2, Y is derived from water or an organic compound containing x reactive hydrogen atoms, E is a polyoxyethylene moiety constituting at least 60% by weight of the copolymer n has a value such that the minimum molecular weight of A is between about 500 and about 900, as determined by the hydroxyl number of an intermediate,

$$Y[(A)_n-H]_x \quad (II)$$

and the total average molecular weight of the copolymer is at least about 5000.

Preferred are polyoxyalkylene block copolymers of the formula:

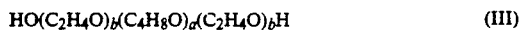

$$HO(C_2H_4O)_b(C_4H_8O)_a(C_2H_4O)_bH \quad (III)$$

wherein in III, a is an integer such that the hydrophobe base represented by $(C_4H_8O)_a$ has a molecular weight of at least about 500 as determined by hydroxyl number, the polyoxyethylene chain constituting at least about 70% by weight of the copolymer, and the copolymer having a total average molecular weight of at least 15,000, or

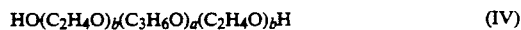

$$HO(C_2H_4O)_b(C_3H_6O)_a(C_2H_4O)_bH \quad (IV)$$

wherein in IV, a is an integer such that the hydrophobe base represented by $(C_3H_6O)_a$ has a molecular weight of at least about 900 average molecular weight, as determined by hydroxyl number, the polyoxyethylene chain constituting at least about 70% by weight of the copolymer, and the copolymer having a total average molecular weight of at least about 15,000, or

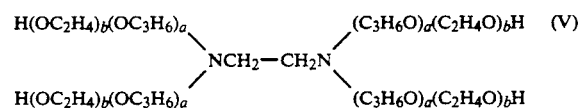

wherein in V, a and b are integers such that the copolymer has a hydrophobe molecular weight of at least about 1500, a hydrophile content of at least about 70%, and a total average molecular weight of at least about 15,000.

Most preferred are the polyoxyalkylene block copolymers of the formula:

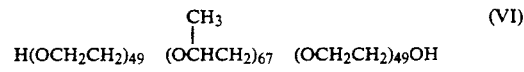

These copolymers are present, preferably, in the amount of about 10 to about 30% by weight of the total weight of the compositions of the invention.

The vehicles for drug delivery of the invention are an improvement over those vehicles used in prior art methods of ophthalmological drug delivery in that the compositions can be optimized for tolerance in the eye by formulating the drug delivery compositions so as to have isotonic characteristics. By matching the osmolality of the drug delivery compositions of the invention to those of the lacrimal fluid of the eye, it is possible to eliminate burning or other discomfort upon application of the drug delivery systems of the invention to the eye. Generally, a pharmacologically effective amount of a drug selected from the group consisting of anti-bacterials, antihistamines and decongestants, anti-inflammatories, miotics and anticholinergics, antiparasitics, mydriatics, antiglaucoma drugs, carbonic anhydrase inhibitors, ophthalmic diagnostic agents, ophthalmic agents used as adjuvants in surgery, chelating agents, antivirals, local anesthetics, antifungals, amoebicidals, trichomonicidals, analgesics, chelating agents, immunosuppressive agents and antimetabolites can be used in conjunction with the polyoxyalkylene block copolymers of the invention. Other drugs or diagnostic agents which can be administered by means of the compositions according to the invention are, for example:

Antibacterial substances such as beta-lactam antibiotics, such as cefoxitin, n-formamidoylthienamycin and other thienamycin derivatives, tetracyclines, chloramphenicol, neomycin, carbenicillin, colistin, penicillin G, polymyxin B, vancomycin, cefazolin, cephaloridine, chibrorifamycin, gramicidin, bacitracin and sulfonamides;

aminoglycoside antibiotics such as gentamycin, kanamycin, amikacin, sisomicin and tobramycin;

nalidixic acid and its analogs such as norfloxacin and the antimicrobial combination fluoroalanine/pentizidone, nitrofurazones and analogs thereof;

antihistaminics and decongestants such as pyrilamine, chlorpheniramine, tetrahydrazoline, antazoline and analogs thereof; mast-cell inhibitors of histamine release, such as cromolyn;

anti-inflammatories such as cortisone, hydrocortisone, hydrocortisone acetate, betamethasone, dexamethasone, dexamethasone sodium phosphate, prednisone, methylprednisolone, medrysone, fluorometholone, prednisolone, prednisolone sodium phosphate, triamcinolone, indomethacin, sulindac, its salts and its corresponding sulfides, and analogs thereof;

miotics and anticholinergics such as echothiophate, pilocarpine, physostigmine salicylate, diisopropylfluorophosphate, epinephrine, dipivaloylepinephrine, neostigmine, echothiopate iodide, demecarium bromide, carbamoyl choline chloride, methacholine, bethanechol, and analogs thereof;

mydriatics such as atropine, homatropine, scopolamine, hydroxyamphetamine, ephedrine, cocaine, tropicamide, phenylephrine, cyclopentolate, oxyphenonium, eucatropine, and analogs thereof;

Other drugs can be used in the treatment of conditions and lesions of the eyes such as:

antiglaucoma drugs, for example, timolol, and especially its maleic salt and R-timolol and a combination of timolol or R-timolol with pilocarpine, as well as many other adrenergic agonists and/or antagonists: epinephrine and an epinephrine complex, or prodrugs such as bitartrate, borate, hydrochloride and dipivefrine derivatives; carbonic anhydrase inhibitors such as acetazolamide, dichlorphenamide, 2-(p-hydroxyphenyl)-thio thiophenesulfonamide, 6-hydroxy-2-benzothiazolesulfonamide, and 6-pivaloyloxy-2-benzothiazolesulfonamide;

antiparasitic compounds and/or anti-protozoal compounds such as ivermectin, pyrimethamine, trisulfapidimidine, clindamycin and corticosteroid preparations;

compounds having antiviral activity such as acyclovir, 5-iodo-2'-deoxyuridine (IDU), adenosine arabinoside (Ara-A), trifluorothymidine, interferon, and interferon-inducing agents such as poly I:C;

antifungal agents such as amphotericin B, nystatin, flucytosine, natamycin and miconazole;

anesthetic agents such as etidocaine cocaine, benoxinate, dibucaine hydrochloride, dyclonine hydrochloride, naepaine, phenacaine hydrochloride, piperocaine, proparacaine hydrochloride, tetracaine hydrochloride, hexylcaine, bupivacaine, lidocaine, mepivacaine and prilocaine;

ophthalmic diagnostic agents, such as:

(a) those used to examine the retina such as sodium fluorescein;

(b) those used to examine the conjunctiva, cornea and lacrimal apparatus, such as fluorescein and rose bengal; and (c) those used to examine abnormal pupillary responses such as methacholine, cocaine, adrenaline, atropine, hydroxyamphetamine and pilocarpine;

ophthalmic agents used as adjuncts in surgery, such as alpha-chymotrypsin and hyaluronidase;

chelating agents such as ethylenediaminetetraacetic acid (EDTA) and deferoxamine;

immunosuppressants and anti-metabolites such as methotrexate, cyclophosphamide, 6-mercaptopurine and azathioprine; combinations of the compounds mentioned above, such as antibiotics/anti-inflammatories combinations such as the combination of neomycin sulfate and dexamethasone sodium phosphate and combinations concomitantly used for treating glaucoma, for example, a combination of timolol maleate and aceclidine.

Preferably the drug delivery compositions of the invention will contain from about 0.01% to about 60% by weight of the medicament or pharmaceutical, and generally from about 10 to about 50% of the polymer and from 80% to about 20% water. In special situations, however, the amounts may be varied to increase or decrease the dosage schedule.

If desired, the drug delivery vehicle or medical device may also contain preservatives, cosolvents, suspending agents, viscosity enhancing agents, ionic-strength and osmolality adjustors and other excipients in addition to buffering agents. Suitable water soluble preservatives which may be employed in the drug delivery vehicle are sodium bisulfite, sodium thiosulfate, ascorbate, benzalkonium chloride, chlorabutanol, thimerosal, phenylmercuric borate, parabens, benzylalcohol phenylethanol and others. These agents may be present, generally, in amounts of about 0.001% to about 5% by weight and, preferably, in the amount of about 0.01 to about 2% by weight.

Suitable water soluble buffering agents are alkali or alkali earth carbonates, phosphates, bicarbonates, citrates, borates, acetates, succinates and the like, such as sodium phosphate, citrate, borate, acetate, bicarbonate, carbonate and tromethamine (TRIS). These agents are present in amounts sufficient to maintain the pH of the system at 7.4±0.2 and preferably, 7.4. As such the buffering agent can be as much as 5% on a weight basis of the total composition.

Many pharmaceutically active materials may be delivered to the eye by the drug delivery system of this invention. Preferably, the drug, or pharmaceutical, is water soluble. Some drugs will show greater solubility in the aqueous polymer system than others. Cosolvents can be used to enhance drug solubility; however, some drugs may be insoluble. These can often be suspended in the polymer vehicle with the aid of suitable suspending or viscosity enhancing agents.

Representative buffering agents or salts useful in maintaining the pH at about 7.4±0.2 are alkali or alkali earth carbonates, chlorides, sulfates, phosphates, bicarbonates, citrates, borates, acetates and succinates. Representative preservatives are sodium bisulfite, sodium thiosulfate, ascorbate, benzalkonium chloride, chlorobutanol, thimerosal, phenylmercuric borate, parabens, benzylalcohol and phenylethanol.

The preparation of the drug delivery vehicles, drug delivery compositions, and medical devices of the invention are described below. The examples which follow were prepared according with the following preparation procedure. Since the polyoxyalkylenes dissolve more completely at reduced temperatures, the preferred methods of solubilization are to add the required amount of polymer to the amount of water to be used. Generally after wetting the polymer by shaking, the mixture is capped and placed in a cold chamber or in a thermostatic container at about 0° C. to 10° C. in order to dissolve the polymer. The pharmacologically active medicaments and various additives such as buffers, salts, and preservatives can subsequently be added and dissolved. In some instances the pharmacologically active substance must be suspended since it is insoluble in water. The pH of 7.4±0.2 is obtained by the addition of appropriate buffering agents.

The following examples illustrate the various aspects of the invention but are not intended to limit its scope. Where not otherwise specified throughout this specification and claims, temperatures are given in degrees centigrade and parts, percentages, and proportions are by weight.

EXAMPLE 1

This Example describes a composition of the invention for ophthalmic use as a surgical aid. The composition prepared was characterized as iso-osmotic, sterile, and having a pH of 7.4±0.2. An aqueous solution was made of a polyoxyethylene-polyoxypropylene block copolymer having the structure generically shown above as Formula IV and having a polyoxypropylene hydrophobe base average molecular weight of about 4000, a total average molecular weight of about 11,500, and containing oxyethylene groups in the amount of about 70% by weight of the total weight of copolymer. This copolymer (Formula VI below) is sold under the trademark PLURONIC ® F-127 (also known as Poloxamer 407) by the BASF Corporation, Parsippany, N.J. A solution in TRIS hydrochloride buffer was made by dissolving said polymer and sodium alginate in cold (4° C.) buffer to give a concentration of 19% by weight polyoxyalkylene and 1% by weight sodium alginate in accordance with the cold process procedure described above for forming aqueous solutions. More specific solution procedures are described in "Artificial Skin I Preparation and Properties of PLURONIC F-127 Gels For Treatment of Burns", *Journal of Biomedical Material Research* 6, 527, 1972, incorporated herein by reference. The block copolymer has the formula:

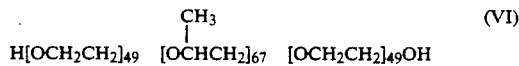

(VI)

This formulation forms the basis for the Figure in which curve A is the determined osmolality of the formulation in the liquid state and curve B is the calculated osmolality of the formulation in the gelled state. It is noted that generally the formulation will gel at mammalian body temperatures only at concentrations of polymer exceeding 17%.

The formulation was sterilized by autoclaving at 121° C. and 15 psi for 15 minutes. The pH before autoclaving was found to be 7.3 and after autoclaving remained the same. The osmolality in the gelled state before autoclaving was determined to be 290±10 and after autoclaving 298±10 mOsm/kg. The gel strength (viscosity) in centipoise as measured at 37° C. using a Brookfield (spindle and cup) viscometer at 20 revolutions per minute was greater than 44,000 before autoclaving and greater than 44,000 after autoclaving.

EXAMPLE 2

This example formulation describes an iso-osmotic, isotonic, pH balanced, thermoreversible system, in which the active ingredient is dissolved. The following antibiotic formulation was prepared to contain 3.5 mg of neomycin sulfate and 10,000 units of polymyxin B sulfate per gram of antibiotic formulation solution. The antibiotic formulation was prepared as follows:

| Ingredient | Percent by Weight |
|---|---|
| Neomycin sulfate | 0.55 |
| Polymyxin B sulfate | 0.12 |
| Glycerin | 0.7 |
| Poloxamer 407 (BASF) | 19.0 |
| Methyl/Propyl Parabens (9:1) | 0.1 |
| TRIS hydrochloride buffer (0.1 molar) | 79.53 |

The formulation was prepared by dissolving the methyl/propyl paraben preservative, neomycin sulfate and polymyxin B sulfate by stirring in the required amount of TRIS hydrochloride buffer. These ingredients in a glass beaker were placed on ice and the Poloxamer 407 was added to the beaker slowly while stirring. After the Poloxamer 407 was completely dissolved, the formulation was stored at 4° C. The product obtained was characterized as clear, colorless and exhibiting gelation at the temperature of mammalian skin (33°±2° C.). The formulation was sterilized by autoclaving for 15 minutes at 15 psi and 121° C. The pH and osmolality of the product were as follows: pH 7.5 and osmolality of approximately 650 mOsm/kg in the liquid state. In the gelled state, the pH and osmolality of the preparation would be expected to be 7.5 and 290 mOsm/kg, respectively.

EXAMPLE 3

This is an example of an iso-osmotic, isotonic, pH balanced, thermoreversible system, in which the active ingredient is dispersed.

The following antibacterial formulation was prepared to contain one percent by weight of silver sulfadiazine.

| Ingredient | Proportions by Weight |
|---|---|
| Silver Sulfadiazine | 1.0 |
| Glycerin | 0.25 |
| Xanthan Gum | 0.33 |
| Poloxamer 407 (BASF) | 18.66 |
| Methyl/Propyl Parabens (9:1) | 0.1 |
| TRIS Maleate Buffer (0.05 molar) | 79.72 |

The formulation was prepared by levigating silver sulfadiazine and glycerin in a glass mortar. Weighed amounts of xanthan gum paste (2.5% in a buffer portion) were added with continued levigation. The Poloxamer 407 and the methyl/propyl paraben preservatives were added to the other buffer portion, in accordance with the cold process described above, to prepare an aqueous solution. This solution was weighed and mixed with a weighed amount of levigated mix. The mixing was achieved with a homogenizer and in a nitrogen environment. The product obtained was characterized as milky-white and exhibiting gelation at the temperature of mammalian skin (33°±2° C.). The pH of the product was 7.32 and the measured osmolality in the liquid state was 573 mOsm/kg. The calculated osmolality in the gelled state was approximately 290 mOsm/kg, assuming that the gelled Poloxamer 407 molecules do not contribute to the osmotic force.

EXAMPLES 4 AND 5

Examples 2 and 3 are repeated substituting 2% by weight of polymer #2, as described in U.S. Pat. No. 4,810,503 and 4% by weight of surfactant #1, as described therein. The balance of the percentage of Poloxamer 407 used in Examples 2 and 3 is made up with TRIS hydrochloride buffer. These formulations form gels at room temperature. Substantially similar pH and osmolality results are obtained.

While this invention has been described with reference to certain specific embodiments, it will be recognized by those skilled in the art that many variations are possible without departing from the scope and spirit of the invention, and it will be understood that it is intended to cover all changes and modifications of the invention, disclosed herein for the purposes of illustration, which do not constitute departures from the spirit and scope of the invention.

The embodiments of the invention in which an exclusive property or privilege is claimed are defined as follows:

1. A hyperosmotic, iso-osmotic, or hypo-osmotic aqueous composition for use as a vehicle for drug delivery, a drug delivery composition, or a medical device for treating an eye condition, where said composition is a liquid at room temperature or below and a gel with a desired osmolality at mammalian body temperature, said aqueous composition containing:

(A) about 10 to about 50% by weight of a polyoxyalkylene block copolymer of formula $$Y[(A)_n-E-H]_x \qquad (I)$$

wherein A is a polyoxyalkylene moiety having an oxygen/carbon atom ratio of less than 0.5, x is at least 1, Y is derived from water or an organic compound containing x reactive hydrogen atoms, E is a polyoxyethylene moiety, n has a value such that the average molecular weight of A is at least about 500, as determined by the hydroxyl number of an intermediate of formula $$Y[(A)_n-H]_x \qquad (II)$$

and the total average molecular weight of the polyoxyalkylene block copolymer is at least about 5000 and (B) about 80% to about 20% by weight of water; wherein the osmolality of the aqueous composition in the liquid state is adjusted to achieve the desired value of the osmolality of the gel by assuming that the polyoxyalkylene block copolymer does not contribute to the osmolality in the gel.

2. The composition of claim 1 wherein said Y in said polyoxyalkylene block copolymer is derived from a water soluble organic compound having 1 to about 6 carbon atoms and wherein said composition further contains a pharmacologically effective amount of a drug selected from the group consisting of antibacterials, decongestants, anti-inflammatories, miotics, mydriatics, antiglaucoma drugs, carbonic anhydrase inhibitors, ophthalmic diagnostic agents, ophthalmic agents used as adjuvants in surgery, chelating agents, local anesthetics, analgesics, immunosuppressive agents and antimetabolites.

3. The composition of claim 1 wherein said Y in said polyoxyalkylene block copolymer is derived from a water soluble organic compound having 1 to about 6 carbon atoms and wherein said composition further contains a pharmacologically effective amount of a drug, wherein said drug is an antihistamine, an anticholinergic, or an antiparasitic, wherein said antiparasitic is selected from the group consisting of antivirals, antifungals, amoebicidals, and trichomonocidals.

4. The composition of claim 1 wherein said polyoxyalkylene moiety is derived from an alkylene oxide selected from the group consisting of butylene oxide, propylene oxide, and mixtures thereof and Y is derived from an organic compound selected from the group consisting of propylene glycol, glycerin, pentaerythritol, trimethylolpropane, ethylenediamine and mixtures thereof.

5. The composition of claim 4 wherein said copolymer is a polyoxyethylene-polyoxypropylene block copolymer wherein said polyoxyethylene moiety constitutes at least about 70% by weight of the copolymer, the average molecular weight of A is at least about 1200, and the total molecular weight of the copolymer is at least about 5,000.

6. The composition of claim 5 wherein the intermediate of Formula II is prepared by initiation with propylene glycol and has a molecular weight of at least about 1500.

7. The composition of claim 6 wherein said polyoxyalkylene block copolymer has the formula $$HO(C_2H_4O)_b(C_4H_8O)_a(C_2H_4O)_bH \qquad (III)$$

wherein a and b are integers such that the hydrophobe base represented by $(C_4H_8O)_a$ has an average molecular weight of at least about 500 as determined by hydroxyl number, the polyoxyethylene chain constituting at least about 70% by weight of the polyoxyalkylene block copolymer, and the polyoxyalkylene block copolymer having a total average molecular weight of at least 15,000; or has the formula $$HO(C_2H_4O)_b(C_3H_6O)_a(C_2H_4O)_bH \qquad (IV)$$

wherein a and b are integers such that the hydrophobe base represented by $(C_3H_6O)_a$ has an average molecular weight of at least about 900, as determined by hydroxyl number, the polyoxyethylene chain constituting at least about 70% by weight of the polyoxyalkylene block copolymer, and the polyoxyalkylene block copolymer having a total average molecular weight of at least 15,000; or has the formula

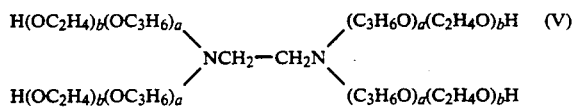

(V)

wherein a and b are integers such that the polyoxyalkylene block copolymer has an average hydrophobe molecular weight of at least about 1500, a hydrophile content of at least about 70% by weight, and a total average molecular weight of at least about 15,000.

8. The composition of claim 7 wherein said polyoxyalkylene block copolymer is

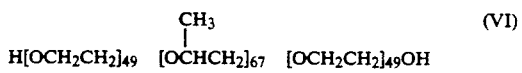

present in the amount of about 10 to about 40% by weight of the total weight of said composition.

9. The composition of claim 7 wherein said polyoxyalkylene block copolymer is present in the amount of about 15 to about 30% by weight in said aqueous composition and wherein the pH is maintained at about 7.4±0.2 and the osmolality in the gel is maintained at about 290 mOsm/kg.

10. A hyperosmotic, iso-osmotic, or hypo-osmotic aqueous composition for use as a vehicle for drug delivery, a drug delivery composition, or a medical device for treating an eye condition, where said aqueous composition is a gel with a desired osmolality at mammalian body temperature, said aqueous composition containing:
a surfactant and
a polyoxyalkylene polyether, said surfactant and said polyoxyalkylene polyether being present in a combined total amount not exceeding about 10% by weight having a molecular weight of about 10,000 to about 100,000 which is selected from the group consisting of
(A) polyoxyalkylene polyethers prepared by reacting ethylene oxide and at least one lower alkylene oxide having 3 to 4 carbon atoms with at least one active hydrogen-containing compound having from 3 to 10 carbon atoms and from 3 to 6 active hydrogens to prepare a heteric or block copolymer intermediate and further reacting said copolymer intermediate with at least one alpha-olefin oxide having an average carbon chain length of about 20 to 45 aliphatic carbon atoms and wherein said alpha-olefin oxide is present in the amount of about 0.3 to 10 percent by weight based upon the total weight of said polyether and
(B) polyoxyalkylene polyethers prepared by reacting ethylene oxide with at least one active hydrogen-containing compound having from 2 to 10 carbon atoms and from 2 to 6 active hydrogens to prepare a homopolymer intermediate and further reacting said homopolymer intermediate with at least one alpha-olefin oxide having an average carbon chain length of about 20 to 45 aliphatic carbon atoms and wherein said alpha-olefin oxide is present in the amount of about 0.3 to 10 percent by weight based on the total weight of said polyether;
wherein the osmolality of the aqueous composition is adjusted to achieve the desired value of the osmolality of the gel by assuming that the polyoxyalkylene polyether does not contribute to the osmolality in the gel.

11. The composition of claim 10 wherein said polyether is prepared using a heteric copolymer intermediate and wherein said aqueous composition further contains a pharmacologically effective amount of a drug selected from the group consisting of antibacterials, decongestants, anti-inflammatories, miotics, mydriatics, antiglaucoma drugs, carbonic anhydrase inhibitors, ophthalmic diagnostic agents, ophthalmic agents used as adjuvants in surgery, chelating agents, local anesthetics, analgesics, immunosuppressive agents and antimetabolites, wherein the drug is present at about 0.01% to 60% by weight based on the total weight of the aqueous composition.

12. The composition of claim 10 wherein said aqueous composition further contains a pharmacologically effective amount of a drug, wherein said drug is an antihistamine, an anticholinergic, or an antiparasitic, wherein said antiparasitic is selected from the group consisting of antivirals, antifungals, amoebicidals, and trichomonocidals, wherein the drug is present at about 0.01% to 60% by weight based on the total weight of the aqueous composition.

13. The composition of claim 10 wherein said polyether is prepared using an alpha-olefin oxide having an average carbon chain length of about 20 to 30 carbon atoms, present in the amount of about 0.3 to 10 percent of the total weight of said polyether.

14. The composition of claim 13 wherein the polyether is prepared using a proportion of ethylene oxide residue to the residue of said lower alkylene oxide of about 70 to about 90 percent by weight of ethylene oxide residue to about 30 to about 10 percent by weight of said lower alkylene oxide residue.

15. The composition of claim 14 wherein said polyether is prepared using propylene oxide as the lower alkylene oxide.

16. The composition of claim 15 wherein said polyether is prepared using a block copolymer intermediate.

17. The composition of claim 16 wherein said polyether is prepared using an alpha-olefin oxide having an average carbon chain length of about 20 to 30 carbon atoms, present in the amount of about 0.3 to 10 percent of the total weight of said polyether.

18. The composition of claim 17 wherein the polyether is prepared using a proportion of ethylene oxide residue to the residue of said lower alkylene oxide of about 70 to about 90 percent by weight of ethylene oxide residue to about 30 to about 10 percent by weight of said lower alkylene oxide residue.

19. The composition of claim 18 wherein said polyether is prepared using propylene oxide as the lower alkylene oxide.

20. The composition of claim 19 wherein said polyether is polyether (B).

21. The composition of claim 10 wherein said polyether is prepared using an alpha-olefin oxide having an average carbon chain length of about 20 to 30 carbon atoms, present in the amount of about 0.3 to 10 percent of the total weight of said polyether and wherein the pH is maintained at about 7.4±0.2 and the osmolality of the gel is maintained at about 290 mOsm/kg.

22. A process for treating an eye condition requiring the use of a medical device or pharmacological treatment which comprises administering to the eye of a mammal a hyperosmotic, iso-osmotic, or hypo-osmotic aqueous composition, where said aqueous composition is a liquid at room temperature or below and a gel with a desired osmolality at mammalian body temperature, said aqueous composition containing:
(A) about 10 to about 50% by weight of a polyoxyalkylene block copolymer of formula

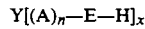

wherein A is a polyoxyalkylene moiety having an oxygen/carbon atom ratio of less than 0.5, x is at least 1, Y is derived from water or an organic compound containing x reactive hydrogen atoms, E is a polyoxyethylene moiety, n has a value such that the average molecular weight of A is at least about 500, as determined by the hydroxyl number of an intermediate of formula $$Y[(A)_n-H]_x \qquad (II)$$

and the total average molecular weight of the polyoxyalkylene block copolymer is at least about 5000 and (B) about 80% to about 20% by weight of water; wherein the osmolality of the aqueous composition in the liquid state is adjusted to achieve the desired value of the osmolality of the gel by assuming that the polyoxyalkylene block copolymer does not contribute to the osmolality in the gel.

23. A process for treating an eye condition requiring the use of a medical device or pharmacological treatment which comprises administering to the eye of a mammal a hyperosmotic, iso-osmotic, or hypo-osmotic aqueous composition, where said aqueous composition is a gel with a desired osmolality at mammalian body temperature, said aqueous composition containing:

a surfactant and a polyoxyalkylene polyether, said surfactant and said polyoxyalkylene polyether being present in a combined total amount not exceeding about 10% by weight having a molecular weight of about 10,000 to about 100,000 which is selected from the group consisting of (A) polyoxyalkylene polyethers prepared by reacting ethylene oxide and at least one lower alkylene oxide having 3 to 4 carbon atoms with at least one active hydrogen-containing compound having from 3 to 10 carbon atoms and from 3 to 6 active hydrogens to prepare a heteric or block copolymer intermediate and further reacting said copolymer intermediate with at least one alpha-olefin oxide having an average carbon chain length of about 20 to about 45 aliphatic carbon atoms and wherein said alpha-olefin oxide is present in the amount of about 0.3 to 10 percent by weight based upon the total weight of said polyether and (B) polyoxyalkylene polyethers prepared by reacting ethylene oxide with at least one active hydrogen-containing compound having from 2 to 10 carbon atoms and from 2 to 6 active hydrogens to prepare a homopolymer intermediate and further reacting said homopolymer intermediate with at least one alpha-olefin oxide having an average carbon chain length of about 20 to about 45 aliphatic carbon atoms and wherein said alpha-olefin oxide is present in the amount of about 0.3 to 10 percent by weight based on the total weight of said polyether;

wherein the osmolality of the aqueous composition is adjusted to achieve the desired value of the osmolality of the gel by assuming that the polyoxyalkylene polyether does not contribute to the osmolality in the gel.

* * * * *